United States Patent [19]

Matsumura et al.

[11] 4,402,948
[45] Sep. 6, 1983

[54] STEROID GLYCOSIDE COMPOUNDS AND METHODS OF USE

[75] Inventors: Shingo Matsumura, Kyoto; Hiroshi Enomoto, Nagaokakyo; Koji Kitaguchi; Masakuni Ozaki, both of Joyo; Masahiko Kitano, Sakyo; Toshihiro Okamura, Makishimacho; Haruo Tanaka, Hikone, all of Japan

[73] Assignee: Nippon Shinyaku Co., Ltd., Japan

[21] Appl. No.: 227,764

[22] Filed: Jan. 23, 1981

[30] Foreign Application Priority Data

Feb. 8, 1980 [JP] Japan .................................. 55-15308

[51] Int. Cl.³ ...................... A61K 31/705; C07J 9/00; C07J 17/00
[52] U.S. Cl. ........................................ 424/182; 536/5
[58] Field of Search ............................ 536/5; 424/182

[56] References Cited

U.S. PATENT DOCUMENTS

| | | | |
|---|---|---|---|
| 4,083,969 | 4/1978 | Inoue et al. | 536/5 |
| 4,157,894 | 6/1979 | Bombardelli | 424/182 |
| 4,188,379 | 2/1980 | Pegel | 424/182 |
| 4,254,111 | 3/1981 | Pegel et al. | 424/182 |
| 4,333,926 | 6/1982 | Ohata et al. | 424/182 |

Primary Examiner—Johnnie R. Brown
Attorney, Agent, or Firm—Jacobs & Jacobs

[57] ABSTRACT

Oxygenated sterylglycoside derivatives of the formula (I) wherein $R_1$, $R_2$, $R_3$ and $R_4$ are the same or different and each is hydrogen or lower alkanoyl, Y is

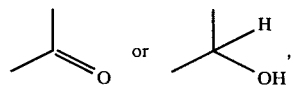

and $R_5$ is 4-methylpentyl, 3-ethyl-4-methylpentyl or 3-ethyl-4-methyl-1-pentenyl are useful for their hemostatic and capillary stabilizing effects.

73 Claims, No Drawings

STEROID GLYCOSIDE COMPOUNDS AND METHODS OF USE

DETAILED DESCRIPTION OF THE INVENTION

Many natural plants having hemostatic effects have been known. It is generally considered that active ingredients of them are tannins, flavones and phospholipids. In the course of the investigations on ingredients of the plant extracts, we have found that the following compounds have hemostatic and capillary-stabilizing effects:

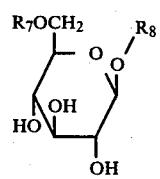

wherein $R_7$ represents hydrogen or palmitoyl group, and $R_8$ represents $\beta$-sitosteryl group, stigmasteryl group or cholesteryl group. After further investigations, we found also that the physiological activities of those sterol glycosides appear in two phases. It is considered that this phenomenon is caused due to effects of the oxygenated metabolites.

We have also determined that the configuration of the sterol side chain in formula (I) is the same as that of $\beta$-sitosterol, stigmasterol and cholesterol and that the configuration is also the same as that of $\beta$-D-glucose and that the configuration of the sugar moiety in formula (I) is the same as that of $\beta$-D-glucose.

On the basis of the above described facts, we made intensive investigations for the purpose of finding compounds which have high physiological activities, are free of side effects peculiar to steroid hormones, are chemically and physically stable and are not readily catabolized in vivo.

After the investigations, we have found that several sterylhexopyranosides (aglycones) having a steroid skeleton in which 7-position has been oxidzed have strong hemostatic and capillary stabilizing effects, their toxicities are only slight and they are scarecely metabolized. The present invention has been completed on the basis of this finding.

Examples of the compounds according to the present invention are shown in Table 1. A process for the preparation of them is shown in Table 2. Their acute toxicity and hemostatic and capillary stabilizing effects are shown in Tables 3–5.

TABLE 1

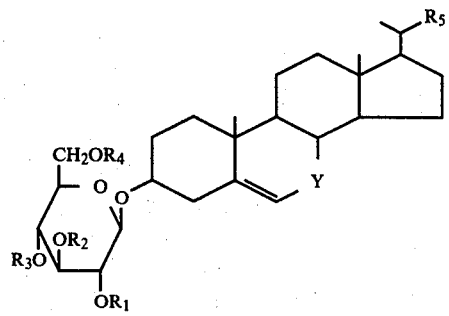

| Compound No. | $R_1$ | $R_2$ | $R_3$ | $R_4$ | Y | $R_5$ |
|---|---|---|---|---|---|---|
| 5 | Ac | Ac | Ac | Ac | =O | 4-methylpentyl |
| 6 | Ac | Ac | Ac | Ac | =O | 3-Ethyl-4-methylpentyl |
| 7 | Ac | Ac | Ac | Ac | =O | 3-Ethyl-4-methyl-l-pentenyl |
| 8 | H | H | H | H | =O | 4-Methylpentyl |
| 9 | H | H | H | H | =O | 3-Ethyl-4-methylpentyl |
| 10 | H | H | H | H | =O | 3-Ethyl-4-methyl-l-pentenyl |
| 11 | Ac | Ac | Ac | Ac | H, OH | 4-Methylpentyl |
| 12 | Ac | Ac | Ac | Ac | H, OH | 3-Ethyl-4-methylpentyl |
| 13 | Ac | Ac | Ac | Ac | H, OH | 3-Ethyl-4-methyl-l-pentenyl |
| 14 | H | H | H | H | H, OH | 4-Methylpentyl |

TABLE 1-continued

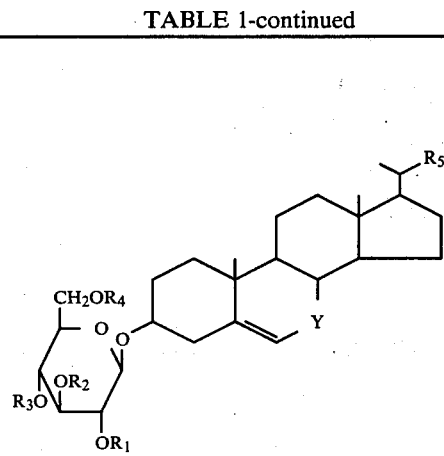

(I)

| Com- pound No. | $R_1$ | $R_2$ | $R_3$ | $R_4$ | Y | $R_5$ |
|---|---|---|---|---|---|---|
| 15 | H | H | H | H | 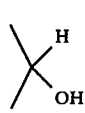 | 3-Ethyl-4-methylpentyl |
| 16 | H | H | H | H | 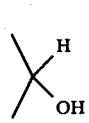 | 3-Ethyl-4-methyl-1-pentenyl |

Ac in the above table represents acetyl group.

TABLE 2

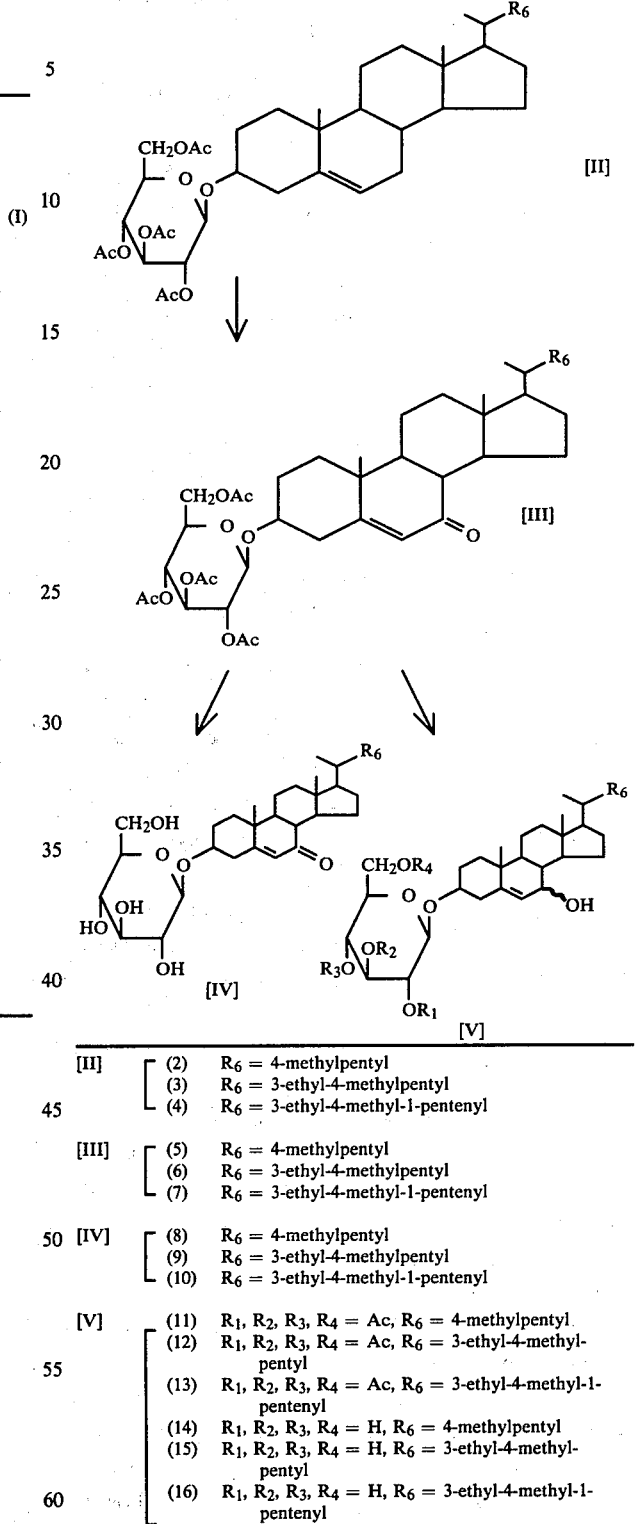

| | | |
|---|---|---|
| [II] | (2) | $R_6$ = 4-methylpentyl |
| | (3) | $R_6$ = 3-ethyl-4-methylpentyl |
| | (4) | $R_6$ = 3-ethyl-4-methyl-1-pentenyl |
| [III] | (5) | $R_6$ = 4-methylpentyl |
| | (6) | $R_6$ = 3-ethyl-4-methylpentyl |
| | (7) | $R_6$ = 3-ethyl-4-methyl-1-pentenyl |
| [IV] | (8) | $R_6$ = 4-methylpentyl |
| | (9) | $R_6$ = 3-ethyl-4-methylpentyl |
| | (10) | $R_6$ = 3-ethyl-4-methyl-1-pentenyl |
| [V] | (11) | $R_1$, $R_2$, $R_3$, $R_4$ = Ac, $R_6$ = 4-methylpentyl |
| | (12) | $R_1$, $R_2$, $R_3$, $R_4$ = Ac, $R_6$ = 3-ethyl-4-methylpentyl |
| | (13) | $R_1$, $R_2$, $R_3$, $R_4$ = Ac, $R_6$ = 3-ethyl-4-methyl-1-pentenyl |
| | (14) | $R_1$, $R_2$, $R_3$, $R_4$ = H, $R_6$ = 4-methylpentyl |
| | (15) | $R_1$, $R_2$, $R_3$, $R_4$ = H, $R_6$ = 3-ethyl-4-methylpentyl |
| | (16) | $R_1$, $R_2$, $R_3$, $R_4$ = H, $R_6$ = 3-ethyl-4-methyl-1-pentenyl |

Compounds (2), (3) and (4) used as starting materials in Table 2 can be obtained as follows:

Thy can be synthesized easily by condensing cholesterol, β-sitosterol and stigmasterol, respectively, with 1-bromo-1-deoxy-2,3,4,6-tetraacetyl-α-D-glucopyranose according to Königs-Knorr method.

Compounds (5), (6) and (7) can be synthesized by oxidizing corresponding starting materials with an excess amount of chromic anhydride in pyridine as solvent.

Those compounds (5), (6) and (7) can be hydrolyzed by a proper method into compounds (8), (9) and (10) and other partial hydrolyzates.

On the other hand, compounds (5), (6) and (7) can be reduced with sodium borohydride into compounds (11), (12) and (13), respectively. Those compounds can further be hydrolyzed by a proper method into compounds (14), (15) and (16) and other partial hydrolyzates.

A. Acute toxicity:

$LD_{50}$ values of oxidized derivatives of steryl-$\beta$-D-glucoside and acetyl derivatives thereof were calculated by Litchfield-Wilcoxon method using male mice.

TABLE 3

| | $LD_{50}$ (mg/Kg) | |
|---|---|---|
| Compound No. | Intraperitoneal administration | Oral administration |
| 5 | >15000 | >12000 |
| 8 | >15000 | >12000 |
| 12 | >15000 | >12000 |
| 16 | >15000 | >12000 |

B. Hemostatic effects:

Influences on bleeding at the end of mouse's tail:

Groups each comprising 10 male mice were employed. According to a method of Motohashi, et al. [Journal of Tokyo Jikei-kai Medical College, 75 (5) (1959)], the end of tail (1 cm) of each mouse was cut out with a sharp surgical knife and the blood threading from the wound into water was observed. A time required until the bleeding stopped completely was measured and rate of readuction of the bleeding time as compared with that of untreated control group was calculated.

TABLE 4

| Compound No. | Dose mg/Kg i.p. | Reduction rate (%) |
|---|---|---|
| 6 | 0.1 | 22 |
| 8 | 0.1 | 36 |
| 11 | 0.1 | 18 |
| 16 | 0.1 | 23 |
| Sodium carbazochromesulfonate | 10.0 | 21 |

C. Capillary stabilizing effects:

Effects of inhibiting hemorrage in mouse's lung:

Degree of hemorrage in mouse's lung caused by pressure reduction to 50±0.5 mmHg/15 sec. was determined by a method of G. J. Mojovski, et al. [J. Pharm. Exp. Therap., 80, 1, (1944)] (score method). From the inhibition rate calculated as compared with untreated control group, $ED_{50}$ of the sample was calculated.

TABLE 5

| Compound No. | $ED_{50}$ (mg/Kg) oral administration |
|---|---|
| 6 | 62 |
| 10 | 43 |
| 14 | 38 |
| Sodium carbazochromesulfonate | >400 |

Thus, it will be understood that the oxidized steryl-glycoside derivatives of the present invention have remarkable hemostatic and capillary stabilizing effects, they exhibit powerful hemostatic effects on the bleeding caused by various factors and they act specifically on the capillary membranes to show capillary-stabilizing and -protective effects even in a very small amount. Therefore, those derivatives can be used as hemostatic agents of quite low toxicity which are effective on bleeding due to various causes or as long lasting capillary-stabilizing remedies for functional disorders in peripheral blood vessels caused by an increase in capillary permeability due to weakened blood vessels.

Those compounds can be used in the form of an injection or intraoral drug (solid). For example, they are used as follows:

| Injection: | |
|---|---|
| Compound 8 | 20 mg |
| NIKKOL HCO-60* | 1.2 g |
| Ethyl alcohol | 10 ml. |
| Glucose | 5 g |

Distilled water for injection is added to the above compounds to make the total quantity 100 ml.

The injection is used one to several times a day each in a dose of 2-10 ml.

| | |
|---|---|
| Compound 8 | 100 mg |
| NIKKOL HCO-60* | 4 g |
| Ethyl alcohol | 5 ml. |
| Common salt | 0.9 g |

*Polyoxyethylene(60)-hydrogenated castor oil.

Distilled water for injection is added to the above compounds to make the total quantity 100 ml.

The injection is used one to several times a day each in a dose of 1-10 ml.

| Powder: | |
|---|---|
| Compound 11 | 1 g |
| Lactose | 99 g |

300 mg-1 g/day is taken several times a day.

| Tablets: | |
|---|---|
| Compound 5 | 2.0 mg |
| Lactose | 20 mg |
| Avicel | 20 m mg |
| Magnesium stearate | 0.2 mg |
| Starch | 7.8 mg |

2-6 Tablets/day are taken several times a day.

The present invention will be illustrated by way of examples, which by no means limit the present invention.

EXAMPLE 1

Preparation of (7-Ketocholesteryl)-2,3,4,6-tetra-0-acetyl-$\beta$-D-glucopyranoside(5)

5.0 Grams of cholesteryl-2,3,4,6-tetra-0-acetyl-$\beta$-D-glucopyranoside(2) was dissolved in 100 ml. of carbon tetrachlofide. The resulting solution was added with 10 ml. of acetic acid and 2.6 ml. of acetic anhydride, then heated to 55°-60° C. and stirred for 45 minutes. Then, a solution prepared by adding 10 ml. of acetic acid and 2.6 ml. of acetic anhydride to a solution of t-butyl chromate (prepared from 6.8 g of chromic acid anhydride and 20 ml. of t-butanol) in carbon tetrachloride was added dropwise thereto. After completion of the addition, the reaction mixture was stirred at that temperature for 24 hours. The reaction mixture was cooled to 20° C. and slowly added with 200 ml. of 10% aqueos oxalic acid solution. The mixture was stirred for one hour and divided into layers. The aqueous layer was extracted with chloroform and the extract was combined with the carbon tetrachloride layer. The organic solvent layer was washed with 5% aqueous sodium bicarbonate solution and saturated sodium chloride salt solution, and then dried with magnesium sulfate. The solvent was then distilled out. The residue was chromatographed on silica gel to give the intended product from a fraction eluted with a solvent mixture of benzene, n-hexane and acetone (3:3:1). After the recrystallization from ethanol, colorless crystals of a melting point of 156.4° C. were obtained in a yield of 50%.

Physical Properties

1. Melting point: 156.4° C.
2. Infrared absorption spectrum $\nu_{max}^{KBr}$ cm$^{-1}$: 1750, 1680.
3. Mass spectrum m/e: 730 (M+).
4. Optical rotation $[\alpha]_D^{24}$: −58.2° (chloroform).

| 5. Elementary analysis as $C_{41}H_{62}O_{11}$: | | |
|---|---|---|
| | C % | H % |
| Theoretical: | 67.19 | 8.80 |
| Found: | 66.72 | 8.78 |

EXAMPLE 2

Preparation of
(7-Ketocholesteryl)-β-D-glucopyranoside (8)

1.00 g of 7-ketocholesteryl-2,3,4,6-tetra-0-acetyl-β-D-glycopyranoside(5) was dissolved in a solvent mixture of methanol and dioxane (5:1). A solution of 40 mg of potassium carbonate in 20 ml. of water was added dropwise thereto with stirring at room temperature. The reaction mixture was stirred at room temperature for 1.5 hours and poured into ice-water. The crystals thus formed were filtered out. The crystals were washed with water and acetone and then recrystallized from dioxane to give 510 mg of the intended compound as colorless crystals. Yield: 66%.

Physical Properties

1. Melting point: 278.0° C.
2. Infrared absorption spectrum $\nu_{max}^{KBr}$ cm$^{-1}$: 3400, 1660.
3. Mass spectrum m/e: 562 (M+).
4. Optical rotation $[\alpha]_D^{24}$: −83.8° (pyridine).

| 5. Elementary analysis as $C_{33}H_{54}O_7$: | | |
|---|---|---|
| | C % | H % |
| Theoretical: | 70.43 | 9.67 |
| Found: | 69.22 | 10.04 |

EXAMPLE 3

Preparation of
(7-hydroxycholesteryl)-2,3,4,6-tetra-0-acetyl-β-D-glucopyranoside(11)

4.0 Grams of (7-ketocholesteryl)-2,3,4,6-tetra-0-acetyl-β-D-glucopyranoside(8) was dissolved in 500 ml. of a mixture of methanol and tetrahydrofuran (3:1). 2.0 Grams of sodium borohydride was added to the solution at −5° C. with stirring and the mixture was stirred at that temperature for 2 hours. The reaction mixture was poured into 500 ml. of ether, added with 7% aqueous acetic acid solution to decompose excessive sodium borohydride and divided into layers. The organic solvent layer was washed with 5% aqueous sodium bicarbonate solution, saturated sodium chloride solution and water and then dried with magnesium sulfate. The solvent was then distilled out. The remaining crystalline substance was chromatographed on silica gel to yield intended product (11) as a single compound from a fraction eluted with a solvent mixture of benzene and ether (9:1-6:4). After recrystallization from ether or isopropyl ether, colorless crystals were obtained. Yield: 61%.

Physical Properties

1. Melting point: 163.0° C.
2. Infrared absorption spectrum $\nu_{max}^{KBr}$ cm$^{-1}$: 3500, 1760.
3. Mass spectrum m/e: 732 (M+).
4. Optical rotation $[\alpha]_D^{24}$: −16.1° (chloroform)

| 5. Elementary analysis as $C_{41}H_{64}O_{11}$: | | |
|---|---|---|
| | C % | H % |
| Theoretical: | 67.18 | 8.80 |
| Found: | 66.64 | 8.85 |

EXAMPLE 4

Preparation of
(7-Hydroxycholesteryl)-β-D-glucopyranoside(14)

1.98 Grams of (7-hydroxycholesteryl)-2,3,4,6-tetra-0-acetyl-β-D-glucopyranoside(11) was hydrolyzed with potassium carbonate in the same manner as in Example 2 to obtain 690 mg of intended product (14). Yield: 45%.

Physical Properties

1. Melting point: 224.5° C. (recrystallized from dioxan)
2. Infrared absorption spectrum $\nu_{max}^{KBr}$ cm$^{-1}$: 3500

| 3. Elementary analysis as $C_{33}H_{56}O_7$: | | |
|---|---|---|
| | C % | H % |
| Theoretical: | 70.17 | 9.99 |
| Found: | 69.63 | 10.32 |

Other compounds of the present invention can be synthesized in the same manner as above. Properties of those compounds are shown in Table 6.

TABLE 6

| Compound No. | m.p. (C.) | Optical rotation [α]_D (Solvent) | Molecular formula | Values of elementary analysis (Upper column: Theoretical Lower column: Found) Carbon (%), Hydrogen (%) |
|---|---|---|---|---|
| 6 | 150.6° | −62.9° (Chloroform) | $C_{43}H_{58}O_{11}$ | 68.04, 8.77 <br> 67.97, 9.18 |
| 7 | 135.1° | −67.1° (Chloroform) | $C_{43}H_{64}O_{11}$ | 68.23, 8.52 <br> 67.80, 8.94 |
| 9 | 265° | −79.7° (Pyridine) | $C_{35}H_{58}O_7.\frac{1}{2}H_2O$ | 70.08, 9.91 <br> 70.09, 10.35 |
| 10 | 200~205° | −80.8° (Pyridine) | $C_{35}H_{58}O_7.4H_2O$ | 63.61, 9.76 <br> 63.94, 9.62 |
| 12 | 121~122° | — | $C_{43}H_{58}O_{11}$ | 68.04, 9.01 <br> 67.76, 9.49 |
| 13 | 156.6~7.4° | −20.2° (Chloroform) | $C_{43}H_{58}O_{11}$ | 68.04, 8.76 <br> 68.03, 9.01 |
| 15 | 220~225° | −10.2° (Pyridine) | $C_{35}H_{60}O_7.H_2O$ | 68.82, 10.23 <br> 68.14, 10.31 |
| 16 | 209.4~210.2° (Decomp.) | — | $C_{35}H_{58}O_7$ | 71.15, 9.90 <br> 69.39, 10.21 |

We claim:

1. An oxygenated sterylglycoside derivative of the formula (I):

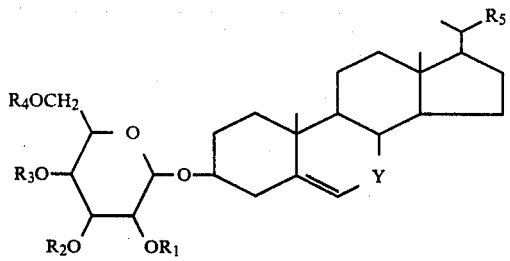

wherein $R_1$, $R_2$, $R_3$ and $R_4$ are the same or different and each is hydrogen or lower alkanoyl, Y is

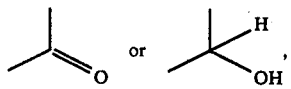

and $R_5$ is 4-methylpentyl, 3-ethyl-4-methylpentyl or 3-ethyl-4-methyl-1-pentenyl.

2. A compound according to claim 1 wherein the configuration of the sterol side chain in formula (I) is the same as that of β-sitosterol.

3. A compound according to claim 1 wherein the configuration of the sterol side chain in formula (I) is the same as that of stigmasterol.

4. A compound according to claim 1 wherein the configuration of the sterol side chain in formula (I) is the same as that of cholesterol.

5. A compound according to claim 1 wherein the configuration of the sugar moiety in formula (I) is the same as that of β-D-glucose.

6. A compound according to claim 2 wherein the configuration of the sugar moiety in formula (I) is the same as that of β-D-glucose.

7. A compound according to claim 3 or 4 wherein the configuration of the sugar moiety in formula (I) is the same as that of β-D-glucose.

8. The compound according to claim 1 which is (7-Ketocholesteryl)-2,3,4,6-tetra-0-acetyl-β-D-glucopyranoside.

9. The compound according to claim 1 which is (7-Ketocholesteryl)-β-D-glucopyranoside.

10. The compound according to claim 1 which is (7-Hydroxycholesteryl)-2,3,4,6-tetra-0-acetyl-β-D-glucopyranoside.

11. The compound according to claim 1 which is (7-Hydroxycholesteryl)-β-D-glucopyranoside.

12. A pharmaceutical composition useful for effecting hemostatic and capillary stabilizing effects which comprises a hemostatically effective amount or a capillary stabilizing effective amount of a compound of the formula (I):

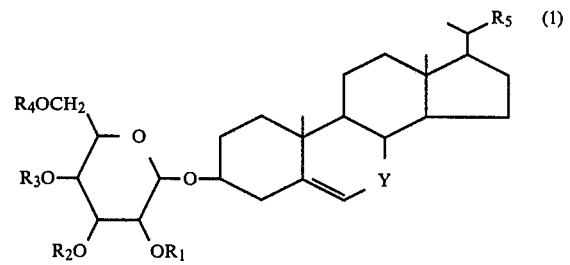

wherein $R_1$, $R_2$, $R_3$ and $R_4$ are the same or different and each is hydrogen or lower alkanoyl, Y is

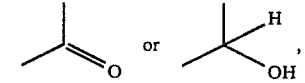

and $R_5$ is 4-methylpentyl, 3-ethyl-4-methylpentyl or 3-ethyl-4-methyl-1-pentenyl, in combination with a pharmaceutically acceptable carrier.

13. A composition according to claim 12 wherein the configuration of the sterol side chain in formula (I) is the same as that of β-sitosterol.

14. A composition according to claim 12 wherein the configuration of the sterol side chain in formula (I) is the same as that of stigmasterol.

15. A composition according to claim 12 wherein the configuration of the sterol side chain in formula (I) is the same as that of cholesterol.

16. A composition according to claim 12 wherein the configuration of the sugar moiety in formula (I) is the same as that of β-D-glucose.

17. A composition according to claim 13 wherein the configuration of the sugar moiety in formula (I) is the same as that of β-D-glucose.

18. A composition according to claim 14 or 15 wherein the configuration of the sugar moiety in formula (I) is the same as that of β-D-glucose.

19. A composition according to claim 12 wherein the compound is (7-Ketocholesteryl)-2,3,4,6-tetra-0-acetyl-β-D-glucopyranoside.

20. A composition according to claim 12 wherein the compound is (7-Ketocholesteryl)-6,2-D-glucopyranoside.

21. A composition according to claim 12 wherein the compound is (7-Hydroxycholesteryl)-2,3,4,6-tetra-0-acetyl-β-D-glucopyranoside.

22. A composition according to claim 12 wherein the compound is (7-Hydroxycholesteryl)-β-D-glucopyranoside.

23. A composition according to claim 12 in oral administration form.

24. A composition according to claim 12 in a form suitable for administration by injection.

25. A method useful for effecting hemostatic or capillary stabilizing effects which comprises administering to one in need thereof, a hemostatically effective amount or a capillary stabilizing effective amount of a compound of the formula (I):

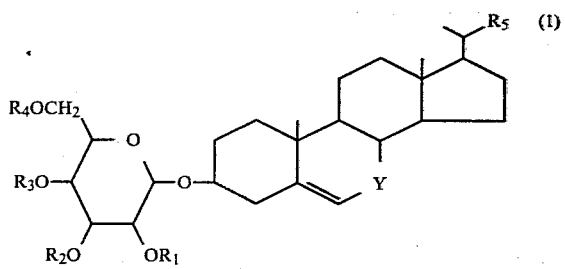

wherein $R_1$, $R_2$, $R_3$ and $R_4$ are the same or different and each is hydrogen or lower alkanoyl, Y is

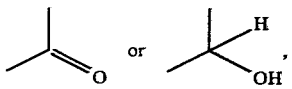

and $R_5$ is 4-methylpentyl, 3-ethyl-4-methylpentyl or 3-ethyl-4-methyl-1-pentenyl, in combination with a pharmaceutically acceptable carrier.

26. A method according to claim 25 wherein the configuration of the sterol side chain in formula (I) is the same as that of β-sitosterol.

27. A method according to claim 25 wherein the configuration of the sterol side chain in formula (I) is the same as that of stigmasterol.

28. A method according to claim 25 wherein the configuration of the sterol side chain in formula (I) is the same as that of cholesterol.

29. A method according to claim 25 wherein the configuration of the sugar moiety in formula (I) is the same as that of β-D-glucose.

30. A method according to claim 26 wherein the configuration of the sugar moiety in formula (I) is the same as that of β-D-glucose.

31. A method according to claim 27 or 28 wherein the configuration of the sugar moiety in formula (I) is the same as that of β-D-glucose.

32. A method according to claim 25 wherein the compound is (7-Ketocholesteryl)-2,3,4,6-tetra-0-acetyl-β-D-glucopyranoside.

33. A method according to claim 25 wherein the compound is (7-Ketocholesteryl)-β-D-glucopyranoside.

34. A method according to claim 25 wherein the compound is (7-Hydroxycholesteryl)-2,3,4,6-tetra-0-acetyl-β-D-glucopyranoside.

35. A method according to claim 25 wherein the compound is (7-Hydroxycholesteryl)-β-D-glucopyranoside.

36. A method according to claim 25 wherein the administration is oral.

37. A method according to claim 25 wherei the compound is in a form suitable for administration by injection.

38. The compound according to claim 1 wherein $R_1$, $R_2$, $R_3$ and $R_4$ are each acetyl, Y is $>=O$ and $R_5$ is 4-methylpentyl.

39. The compound according to claim 1 wherein $R_1$, $R_2$, $R_3$ and $R_4$ are each acetyl, Y is $>=O$ and $R_5$ is 3-ethyl-4-methylpentyl.

40. The compound according to claim 1 wherein $R_1$, $R_2$, $R_3$ and $R_4$ are each acetyl, Y is $>=O$ and $R_5$ is 3-ethyl-4-methyl-1-pentyl.

41. The compound according to claim 1 wherein $R_1$, $R_2$, $R_3$ and $R_4$ are each hydrogen, Y is $>=O$ and $R_5$ is 4-methylpentyl.

42. The compound according to claim 1 wherein $R_1$, $R_2$, $R_3$ and $R_4$ are each hydrogen, Y is $>=O$ and $R_5$ is 3-ethyl-4-methylpentyl.

43. The compound according to claim 1 wherein $R_1$, $R_2$, $R_3$ and $R_4$ are each hydrogen, Y is $>=O$ and $R_5$ is 3-ethyl-4-methyl-1-pentenyl.

44. The compound according to claim 1 wherein $R_1$, $R_2$, $R_3$ and $R_4$ are each acetyl, Y is

and $R_5$ is 4-methylpentyl.

45. The compound according to claim 1 wherein $R_1$, $R_2$, $R_3$ and $R_4$ are each acetyl, Y is

and $R_5$ is 3-ethyl-4-methylpentyl.

46. The compound according to claim 1 wherein $R_1$, $R_2$, $R_3$ and $R_4$ are each acetyl, Y is

and $R_5$ is 3-ethyl-4-methyl-1-pentenyl.

47. The compound according to claim 1 wherein $R_1$, $R_2$, $R_3$ and $R_4$ are each hydrogen, Y is

and $R_5$ is 4-methylpentyl.

48. The compound according to claim 1 wherein $R_1$, $R_2$, $R_3$ and $R_4$ are each hydrogen, Y is

and $R_5$ is 3-ethyl-4-methylpentyl.

49. The compound according to claim 1 wherein $R_1$, $R_2$, $R_3$ and $R_4$ are each hydrogen, Y is

and $R_5$ is 3-ethyl-4-methyl-1-pentenyl.

50. A composition according to claim 12 wherein $R_1$, $R_2$, $R_3$ and $R_4$ are each acetyl, Y is >=O and $R_5$ is 4-methylpentyl.

51. A composition according to claim 12 wherein $R_1$, $R_2$, $R_3$ and $R_4$ are each acetyl, Y is >=O and $R_5$ is 3-ethyl-4-methylpentyl.

52. A composition according to claim 12 wherein $R_1$, $R_2$, $R_3$ and $R_4$ are each acetyl, Y is >=O and $R_5$ is 3-ethyl-4-methyl-1-pentyl.

53. A composition according to claim 12 wherein $R_1$, $R_2$, $R_3$ and $R_4$ are each hydrogen, Y is >=O and $R_5$ is 4-methylpentyl.

54. A composition according to claim 12 wherein $R_1$, $R_2$, $R_3$ and $R_4$ are each hydrogen, Y is >=O and $R_5$ is 3-ethyl-4-methylpentyl.

55. A composition according to claim 12 wherein $R_1$, $R_2$, $R_3$ and $R_4$ are each hydrogen, Y is >=O and $R_5$ is 3-ethyl-4-methyl-1-pentenyl.

56. A composition according to claim 12 wherein $R_1$, $R_2$, $R_3$ and $R_4$ are each acetyl, Y is

and $R_5$ is 4-methylpentyl.

57. A composition according to claim 12 wherein $R_1$, $R_2$, $R_3$ and $R_4$ are each acetyl, Y is

and $R_5$ is 3-ethyl-4-methylpentyl.

58. A composition according to claim 12 wherein $R_1$, $R_2$, $R_3$ and $R_4$ are each acetyl, Y is

and $R_5$ is 3-ethyl-4-methyl-1-pentenyl.

59. A composition according to claim 12 wherein $R_1$, $R_2$, $R_3$ and $R_4$ are each hydrogen, Y is

and $R_5$ is 4-methylpentyl.

60. A composition according to claim 12 wherein $R_1$, $R_2$, $R_3$ and $R_4$ are each hydrogen, Y is

and $R_5$ is 3-ethyl-4-methylpentyl.

61. A composition according to claim 12 wherein $R_1$, $R_2$, $R_3$ and $R_4$ are each hydrogen, Y is

and $R_5$ is 3-ethyl-4-methyl-1-pentenyl.

62. A method according to claim 25 wherein $R_1$, $R_2$, $R_3$ and $R_4$ are each acetyl, Y is >=O and $R_5$ is 4-methylpentyl.

63. A method according to claim 25 wherein $R_1$, $R_2$, $R_3$ and $R_4$ are each acetyl, Y is >=O and $R_5$ is 3-ethyl-4-methylpentyl.

64. A method according to claim 25 wherein $R_1$, $R_2$, $R_3$ and $R_4$ are each acetyl, Y is >=O and $R_5$ is 3-ethyl-4-methyl-1-pentyl.

65. A method according to claim 25 wherein $R_1$, $R_2$, $R_3$ and $R_4$ are each hydrogen, Y is >=O and $R_5$ is 4-methylpentyl.

66. A method according to claim 25 wherein $R_1$, $R_2$, $R_3$ and $R_4$ are each hydrogen, Y is >=O and $R_5$ is 3-ethyl-4-methylpentyl.

67. A method according to claim 25 wherein $R_1$, $R_2$, $R_3$ and $R_4$ are each hydrogen, Y is >=O and $R_5$ is 3-ethyl-4-methyl-1-pentenyl.

68. A method according to claim 25 wherein $R_1$, $R_2$, $R_3$ and $R_4$ are each acetyl, Y is

and $R_5$ is 4-methylpentyl.

69. A method according to claim 25 wherein $R_1$, $R_2$, $R_3$ and $R_4$ are each acetyl, Y is

and $R_5$ is 3-ethyl-4-methylpentyl.

70. A method according to claim 25 wherein $R_1$, $R_2$, $R_3$ and $R_4$ are each acetyl, Y is

and R₅ is 3-ethyl-4-methyl-1-pentenyl.
71. A method according to claim 25 wherein $R_1$, $R_2$, $R_3$ and $R_4$ are each hydrogen, Y is
and R₅ is 4-methylpentyl.
72. A method according to claim 25 wherein $R_1$, $R_2$, $R_3$ and $R_4$ are each hydrogen, Y is
and R₅ is 3-ethyl-4-methylpentyl.
73. A method according to claim 25 wherein $R_1$, $R_2$, $R_3$ and $R_4$ are each hydrogen, Y is
and R₅ is 3-ethyl-4-methyl-1-pentenyl.
* * * * *